(12) United States Patent
Santin

(10) Patent No.: US 6,562,057 B2
(45) Date of Patent: May 13, 2003

(54) NASAL BREATHING ASSIST DEVICES

(76) Inventor: Ernest Santin, 2 Bonad Rd., Beverly, MA (US) 01915

( * ) Notice: Subject to any disclaimer, the term of this patent is extended or adjusted under 35 U.S.C. 154(b) by 0 days.

(21) Appl. No.: 09/862,966

(22) Filed: May 22, 2001

(65) Prior Publication Data

US 2002/0177871 A1 Nov. 28, 2002

(51) Int. Cl.⁷ .............................................. A61M 29/00
(52) U.S. Cl. ...................................................... 606/199
(58) Field of Search ................................ 606/191, 196, 606/198, 199, 204.45; D24/106, 110; D27/103, 170, 183; D28/99

(56) References Cited

U.S. PATENT DOCUMENTS

| | | | | | |
|---|---|---|---|---|---|
| 1,256,188 | A | * | 2/1918 | Wilson | ......................... 606/199 |
| 2,010,485 | A | * | 8/1935 | Heath | ........................... 606/199 |
| 2,569,743 | A | * | 10/1951 | Carlock | ....................... 606/199 |
| 2,672,138 | A | * | 3/1954 | Carlock | ................. 128/206.11 |
| 5,665,104 | A | * | 9/1997 | Lee | ........................ 128/200.24 |
| 5,895,409 | A | * | 4/1999 | Mehdizadeh | ................. 606/199 |
| 6,004,342 | A | * | 12/1999 | Filis | ............................ 606/199 |

\* cited by examiner

Primary Examiner—Danny Worrell
Assistant Examiner—Shaun R Hurley
(74) Attorney, Agent, or Firm—McDermott, Will & Emery

(57) ABSTRACT

Various embodiments of devices to reduce or prevent nasal breathing and snoring are provided. In one embodiment, the devices have open tubular elements which are conic-frustum shaped along an axis, having a larger diameter first end and taper toward a second smaller diameter second end. The tubular elements may have passageways that extend transversely through the tubular elements. In another embodiment, the first ends of the tubular elements are connected by coupling element. The coupling element can be a curved strut shape that maintains the tubular elements in a spaced apart, generally parallel relationship. In alternate embodiments, tabs extend from the first end of the tubular elements and are elongated in the direction toward the second end. The tabs may be attached to the first end, or extend from tab supports that extend radially from the first ends.

The user inserts the tubular elements into the nasal passages to increased airflow through the nasal passages during sleep.

8 Claims, 6 Drawing Sheets

NASAL BREATHING ASSIST DEVICES

FIELD OF THE INVENTION

This invention pertains to methods and devices for nasal breathing assist devices, in particular to methods and devices for reducing snoring.

BACKGROUND OF THE INVENTION

Snoring is a condition characterized by rough, loud, rattling breathing or inspiratory noise during sleep or deep coma. The characteristic snoring noise is produced by vibration of the soft palate (the soft tissue in the roof of the mouth near the throat) or vocal chords by inhaled or exhaled air. As the soft palate vibrates, the lips, cheeks, and nostrils may also vibrate, making the snoring louder.

Snoring can be caused by underlying physical or disease conditions that restrict air passages and force the patient to breathe with exaggerated force to move air through narrowed nasal passages. Chronic snoring can be the result of obstruction of larynx, upper airways, a deviated nasal septum, and blockages to the nose and nasal passages. Temporary snoring, or a sudden onset of snoring can be the result of stuffy and swollen mucus membranes, as with a cold or hay fever, or a nasal polyp.

Anatomical deformities in the airway such as such as large tonsils and adenoids, excessive length of the soft palate, or broken or crooked nose, can also diminish the airway size. Fat deposits around the upper airway, as found in obesity, can make the airway smaller. Low muscle tone in the muscles of the tongue and throat, or medications and foods (such as alcohol) that relax these muscles also increase snoring.

Snoring can causes relationship problems between partners, leading to a loss of intimacy and deterioration of relationships. Decreased sleep, or insufficient restful sleep increases irritability, poor memory and concentration and decreased work performance.

A number of methods and devices have been developed to reduce or eliminate snoring. Some devices are external to the patient and can include, buzzer systems and alarms that wake the patient. Special pillows, neck collars, chin braces and head straps have also been tested in an effort to control snoring. When snoring is caused by serious deformity, surgery has been performed to remove anatomical obstructions, such as removing tonsils, or correcting a deviated septum. Occasionally a procedure called UPPP (Uvulopalatopharyngoplasty) is recommended. This procedure acts like an internal facelift, tightening loose tissue. However, the success rate is only 50%. Laser surgery to correct airway defects is also available in some cases.

Other remedies include herbal potions and medications such as decongestants and anti-histamines. Diet and lifestyle changes may also reduce snoring to some degree.

Various devices have been developed that keep the mouth open, the tongue depressed, or nasal passages open. These dental devices can be expensive custom-fit, or inexpensive over-the counter mouth pieces. Adhesive nasal strips, which are applied externally to either side of the nose, have been developed. While these strips may dilate the nasal passages to small degree, they do not work well in patients with anatomical deformities or obstructions in the nose. Air masks that force pressurized air into the mouth and lungs are available. These devices can be cumbersome, unsightly, painful, or expensive, and the patient may abandon these approaches in short time.

SUMMARY OF THE INVENTION

The object of the present invention is to reduce snoring by improving the air flow through the nasal passages. It is a further object to provide devices that improve airflow through the nasal passages during sleep.

One aspect of the invention provides "dual tube" nasal breathing assist devices having a pair of open-ended tubular elements connected together by a coupler element. The tubular elements are preferably conic-frustum shaped along a tube axis, having a relatively large first end and a relatively small second end, and tapering from the first end to the second end along the tube axis. In some embodiments, each tubular element may have passageways extending through the tubular elements transverse to the tube axis. These passageways may be elongated, and extend at least in part in the direction of the tube axes.

The coupler element maintains the tubular element in a generally parallel relationship to each other in a common plane and in a spaced-apart relation which corresponds generally to the separation between the user's nostrils.

In one embodiment, the coupler element is a resilient, nominally curved strut which allows the tube elements to rotate in a plane substantially perpendicular to the tube axes.

In an alternate embodiment, the coupler element is a resilient, nominally curved strut which allows the tube elements to rotate in a plane substantially perpendicular to the tube axes.

In another embodiment, the tubular elements have resilient tabs that extend from the first (i.e., relatively large) end in a direction substantially parallel to the tube axes. The tabs are elongated in the direction of the tube axes.

In another embodiment of the invention, a "single tube" nasal breathing assist device is a single, open-ended, resilient tubular element, adapted for insertion into a user's nostril. The tubular element is conic-frustum shaped, having a relatively large diameter first end and relatively small diameter second end, and a taper extending from the first end to the second end along a tube axis. The tubular element may have passageways extending through the tubular element transverse to the tube axis. In one form, these passageways may be elongated.

In some forms of both the single tube or dual tube embodiments of the invention, the tubular elements have a tab extending from the first (i.e. relatively large) end which extends substantially parallel to the tube axis and is elongated in the direction of the tube axis. In yet another embodiment, each tube element has a tab support extending radially from the first end in a direction substantially perpendicular to the tube axis. At least one resilient tab extends from the tab support, and is elongated in the direction of the tube axis.

Related objects and advantages of the present invention will be apparent from the following description.

BRIEF DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE PREFERRED EMBODIMENTS

The nasal breathing assist devices according to the various aspects of the invention are shown in FIGS. 1, 4, 5A and 5B. These devices overcome the deficiencies in the currently available devices. The illustrated devices are small, inconspicuous in use, and require no special attachments or fittings. The devices are worn inside the nose, so that the nasal passages are kept open from the inside, rather than by external means. This allows the devices to maintain airways in noses where anatomical abnormalities diminish the effectiveness of externally applied strips. The devices can be used alone, or in conjunction with other snore-reducing aids, such as pillows and medicated nasal sprays.

Figure 1:
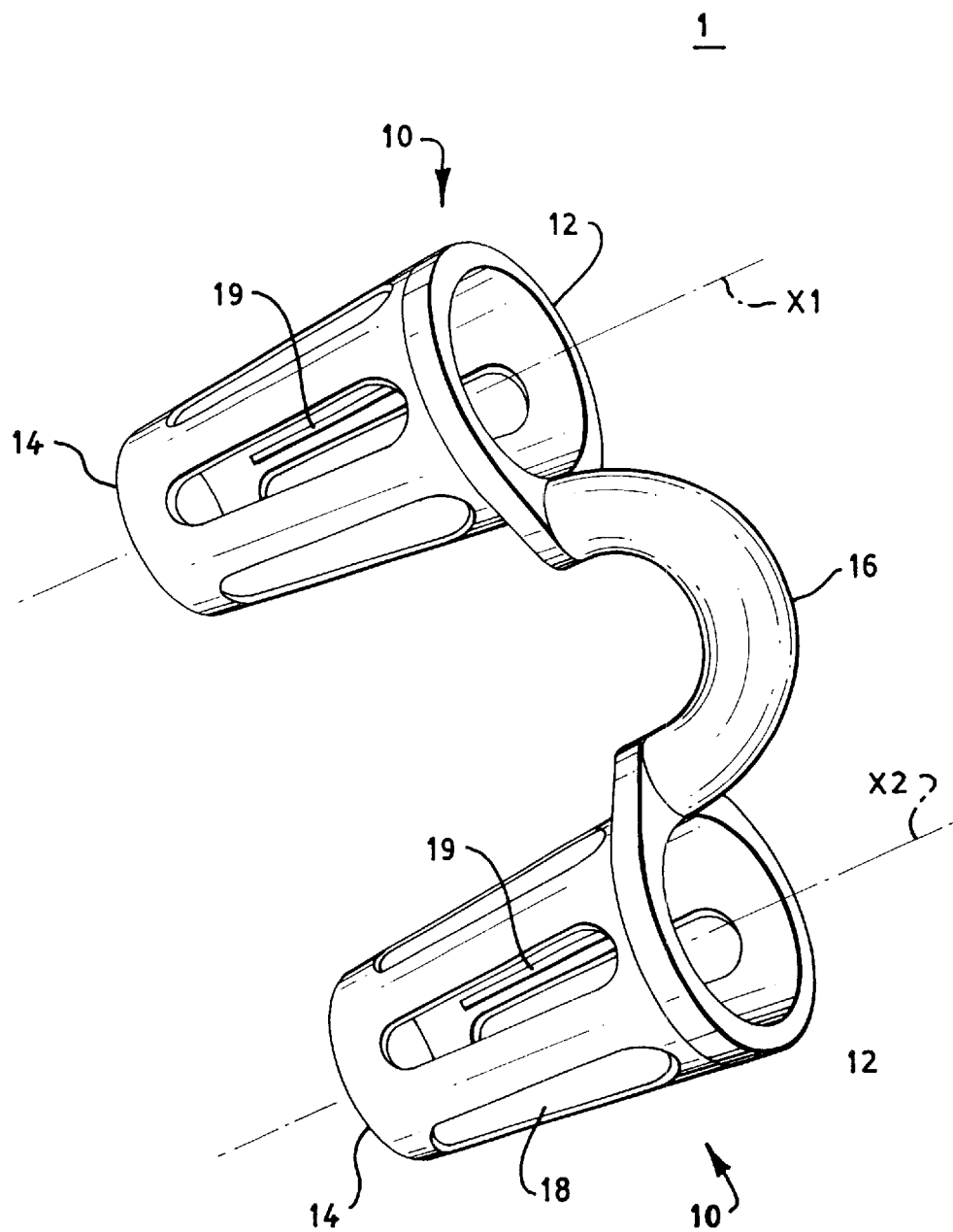
FIG. 1 is a perspective view of one embodiment of the present invention.

In the embodiment shown in FIG. 1, the nasal breathing assist device 1 comprises generally a pair of open ended tubular elements 10 connected together by a coupler element 16.

The tubular elements 10 are generally circular in cross section and extend a distance along tube axes X1 and X2 from first ends 12 to second ends 14. Preferably the tubular elements taper linearly from a relatively large diameter cross section along the tube axes X1 and X2 to a relatively smaller diameter cross section between the first end 12 to second end 14. The taper be other than linear, for example, contoured to correspond generally to the taper inside the user's nostrils. First ends 12 also connect to the coupler element 16. In the illustrated form, the tubular elements 10 are conic-frustums, but other shapes may be used. For example, instead of circular cross sections, the tubular elements could have elliptical or other shaped cross sections. Further, instead of the inner diameter tapering monotonically from the large end to the small end, it could decrease initially, become larger, then decrease again.

The tubular elements 10 may also include at least one passageway 18 extending through the walls of the tubular elements transverse to the tube axes X1 and X2. The passageways 18 may be circular, elliptical, or elongated at least in part in the direction of the tube axes. Alternately, the passageways can be elongated in a direction extending circumferentially around the tube axes.

The coupler element 16 is a resilient, nominally curved strut which maintains the tubular elements spaced apart, with axes X1 and X2 in a substantially parallel relationship, and in substantially a common plane. The coupler element may be made of resilient, semi-rigid, or rigid material.

Grooves 19 inside of tubular elements are an additional features which may be used to receive medication (nasal cream) before inserting in nasal passage so as not to irritate the skin inside the nasal passage, this allows the medication to be effective without contacting the nasal passage.

Figure 2:
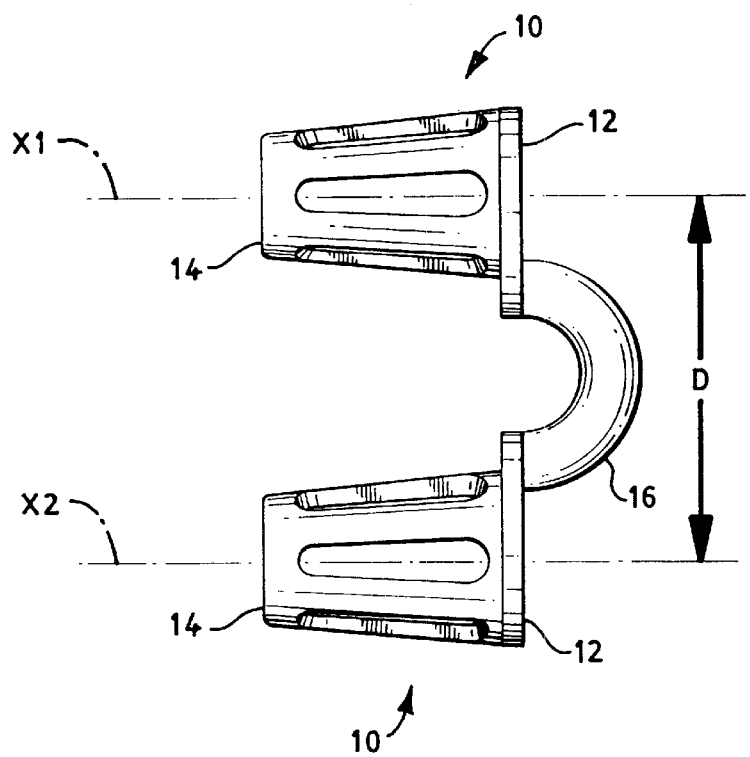
FIG. 2 shows a side view of the embodiment shown in FIG. 1.
Figure 3A:
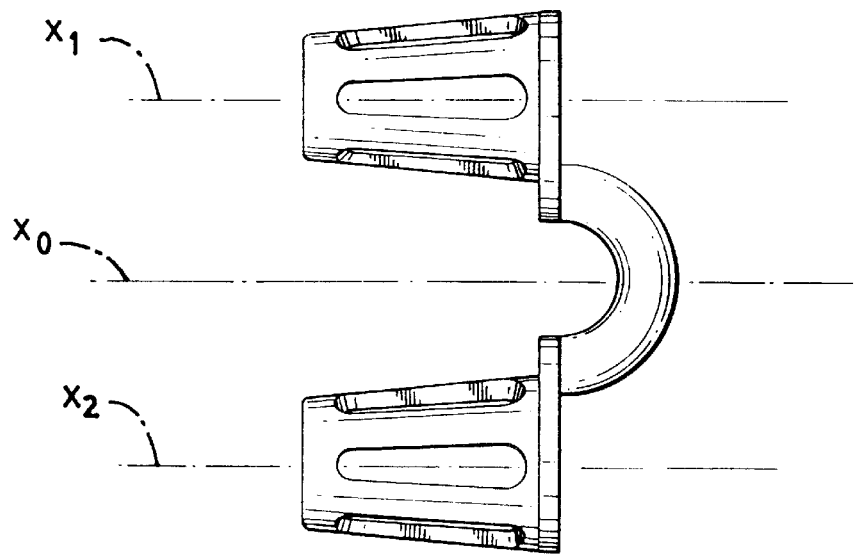
FIG. 3A shows a side view of an alternate embodiment of the invention.
Figure 3B:
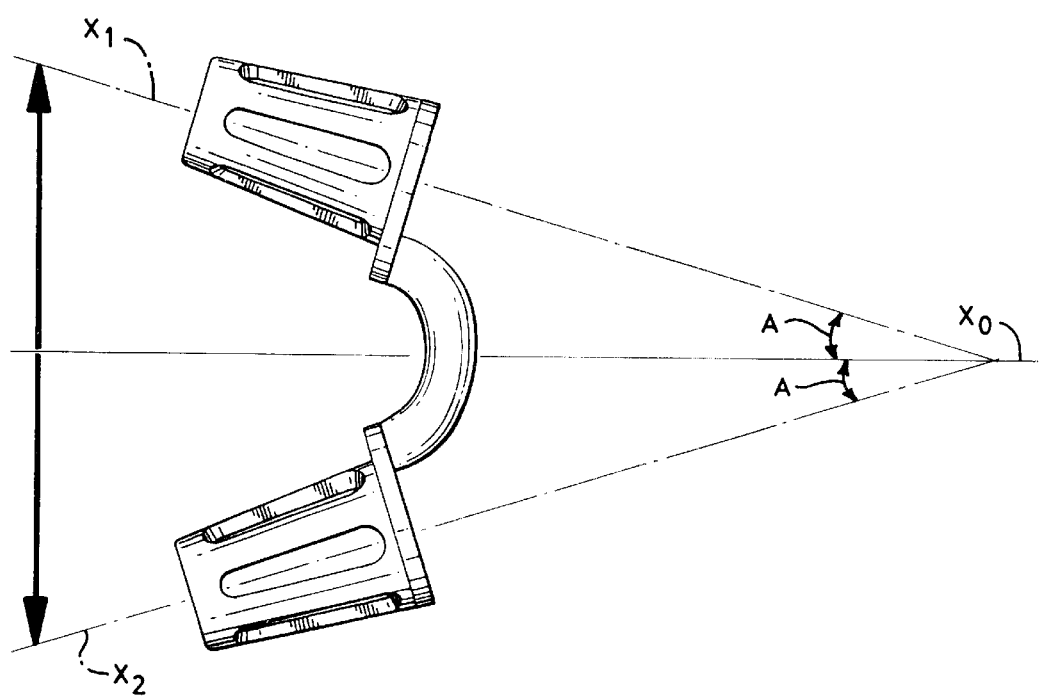
FIG. 3B shows a side view of the embodiment of FIG. 3A rotated about an axis.

As shown in FIG. 2, coupler element 16 maintains a nominal distance D between the tubular elements 10 that generally corresponds to the distance between the user's nostrils. In this embodiment, the coupler element extends in a plane that is essentially parallel to tube axes X1 and X2. As shown in FIGS. 3A and 3B, the resistance of coupler element 16 permits the axes X1 and X2 to be offset from an axis $X_0$ by angle A. Angle A can be as much as 15° or greater. Furthermore, in this embodiment, coupler element 16 permits relative flexing motion of the device about an axis, substantially perpendicular to the tube axes X1 and X2.

Figure 4:
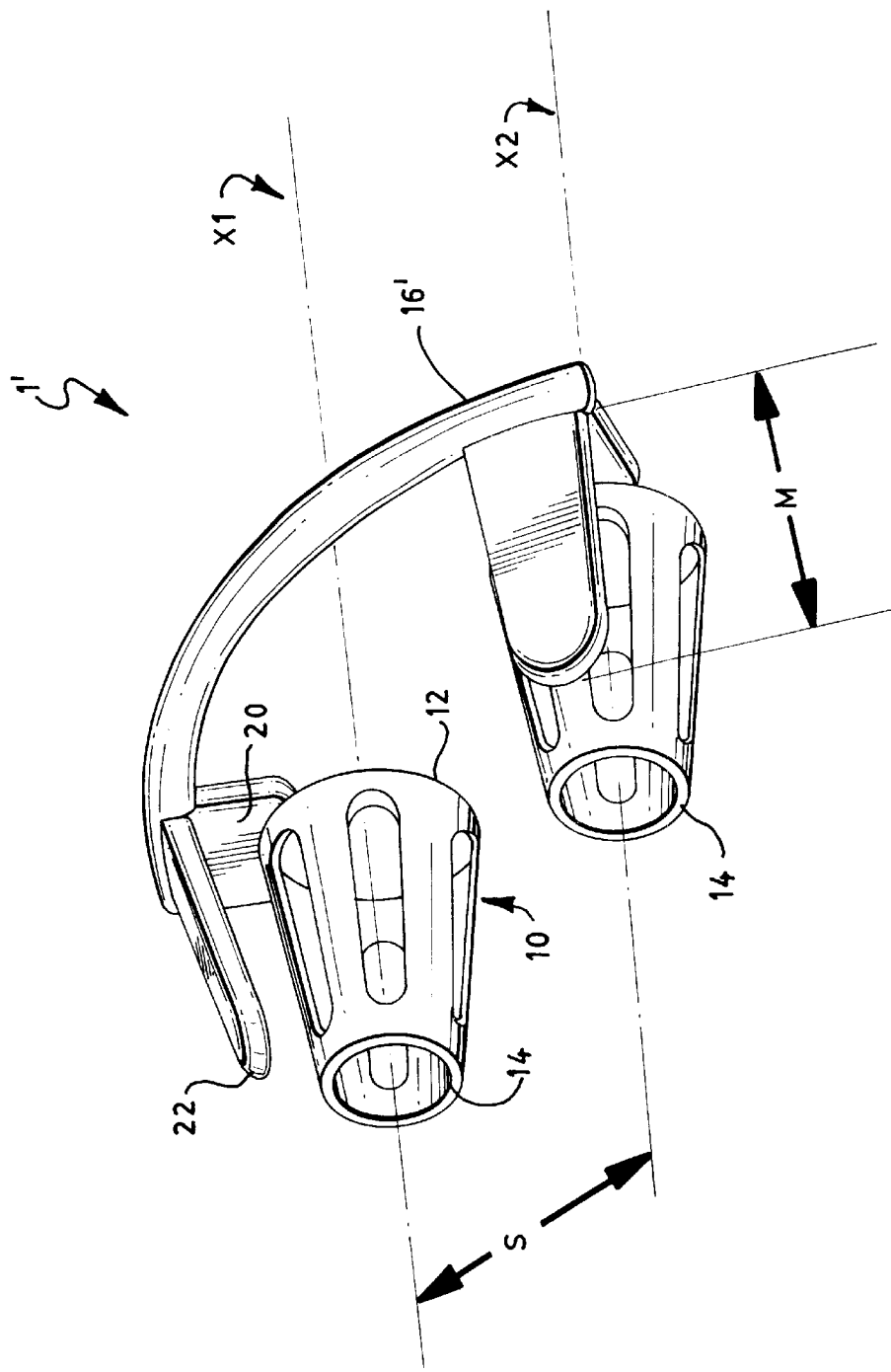
FIG. 4 is a perspective view of an alternate embodiment of the invention.

In a more preferred embodiment shown in FIG. 4, device 1' has coupler element 16' which extends between first ends 12. The central axis of coupler element 16' lies in a plane that is substantially perpendicular to the tube axes X1 and X2. In this embodiment, coupler element 16' permits relative flexing motion of device 1' so that axes X1 and X2 remain substantially parallel, but separation S of those axes varies to accommodate spacing of the nostrils.

Radially extending tab supports 20 extend from first ends 12 and connect to coupler element 16. Tabs 22 extend from tab supports 20 a distance M in the direction of second ends 14. Tabs 22 and tab supports 20 may also made of resilient, semi-resilient, or rigid materials, and may be made of the same or different materials as that used for the tubular elements and coupler elements. In use, tabs 22 remain outside the user's nostrils, and, acting as clips, help secure the device in the nostrils.

Figure 5A:
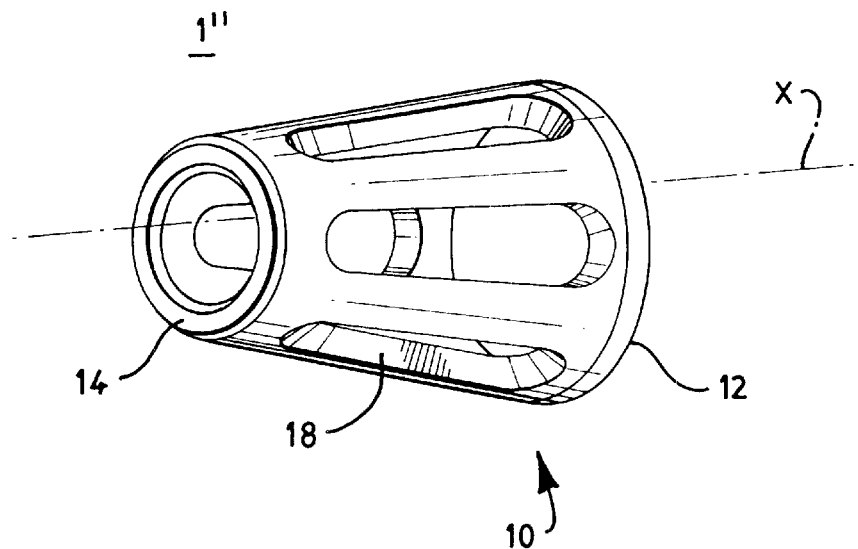
FIG. 5A is a perspective view of an alternate embodiment of the invention.
Figure 5B:
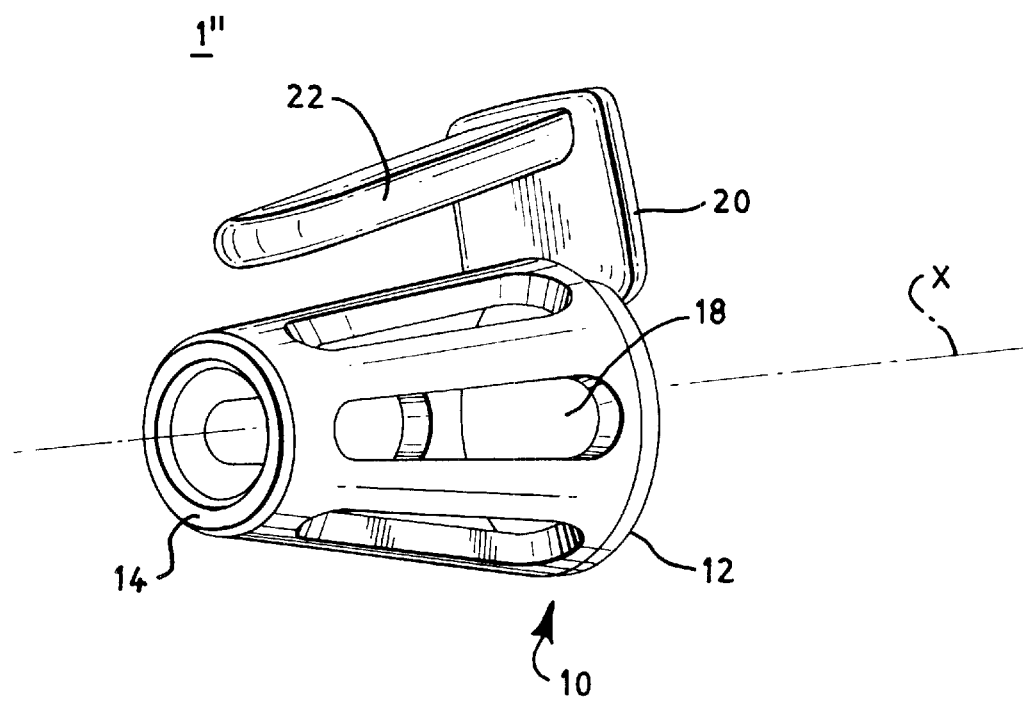
FIG. 5B is a perspective view of yet another embodiment of the invention.

FIGS. 5A and 5B show other embodiments of nasal breathing assist devices. In FIG. 5A, device 1" has a tubular element 10 extending along a tube axis X between a relatively large diameter first end 12 and tapering toward relatively smaller diameter second end 14. As previously described, tubular element 10 may have passageways 18 extending through the walls of the tubular elements transverse to tube axis X.

As shown in the embodiment in FIG. 5B, radially extending tab support 20 extends from first end 12. Tab 22 extends from tab support 20 a distance M in the direction of axis X toward second end 14. Tab 22 helps secure the device in the user's nostrils. Device 1" may be used singly or as a pair.

All of the devices can be made of rigid, semi-resilient, or preferably resilient materials. The nasal breathing assist devices can be disposable or reusable. The reusable devices can be easily cleaned by rinsing with soap and water.

Figure 6:
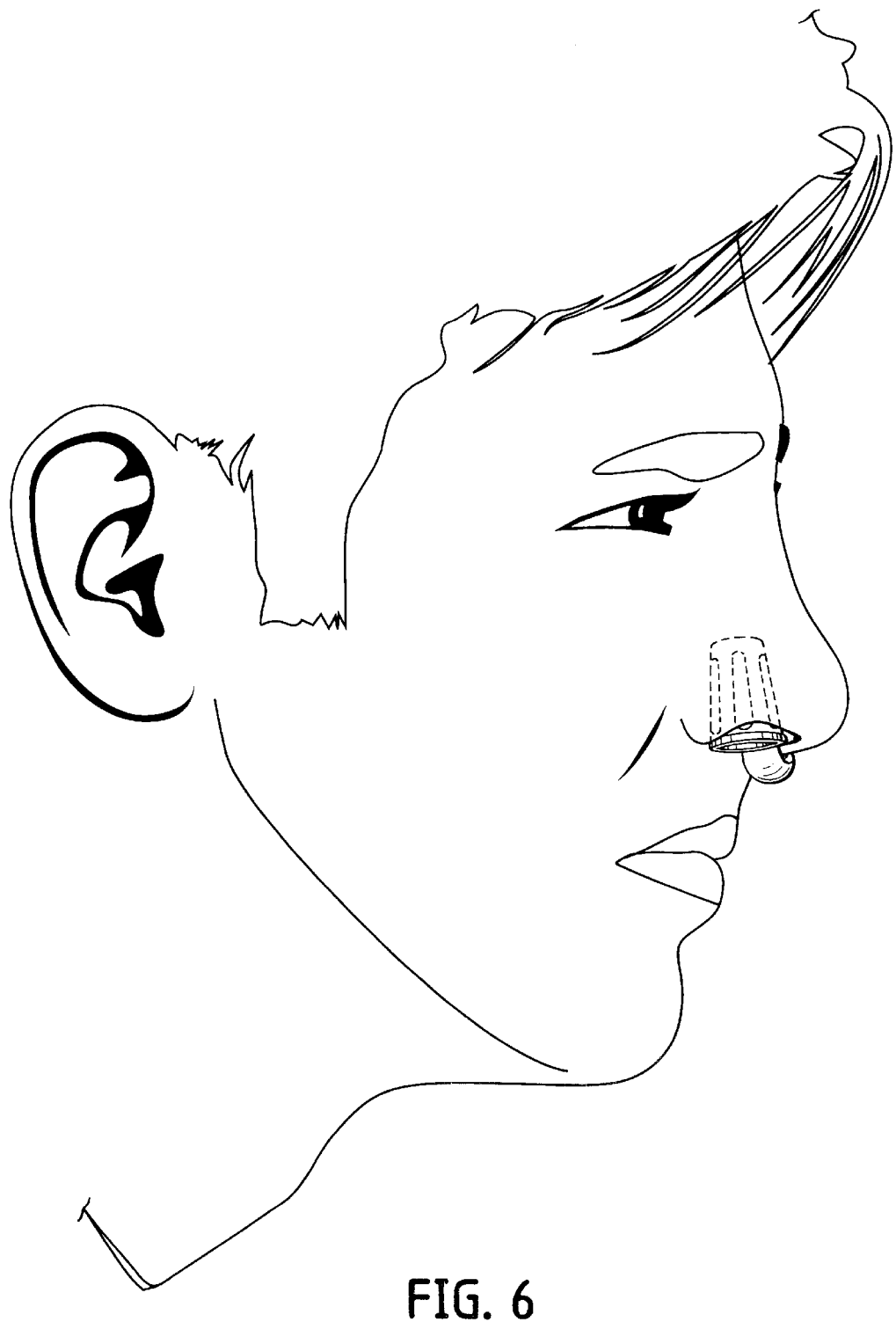
FIG. 6 is a representation of the of one embodiment of the invention in use.

The nasal breathing assist device is inserted in the user's nostrils, as shown in FIG. 6, usually at bedtime. The tubular elements maintain open nasal passages during sleeping, which allows the patient to obtain sufficient airflow through the nose only, rather than supplementing the air supply through the mouth.

The nasal breathing assist devices can be used to aid in the administration of nasally supplied drugs and medications, either at bedtime or during the day. For example, the user can insert the device into the nose, and spray a nasal medication, or moisture mist agent into the nose. The passageways in the device act to help circulate the medication or agent within the nasal passageways by keeping the nasal passages open.

The invention may be embodied on other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

I claim:

1. A nasal breathing assist device comprising:
   i) a pair of open-ended tubular elements, wherein each tubular element extends along a central tube axis between a relatively large first end and a relatively small second end, wherein the axes of said tubular elements lie substantially in a common plane, and
   ii) a coupler element extending between said first ends of said tubular elements, wherein said tube axes of said tubular elements are substantially parallel and spaced apart at said first ends by a distance D, whereby said distance D is selected to correspond nominally to the separation of a user's nostrils, wherein said coupler element is a resilient, nominally curved strut lying substantially in a plane substantially perpendicular to said tube axes, and wherein said coupler element permits relative rotation motion of the axes of the tubular elements.

2. A device according to claim 1 wherein said coupler element permits relative rotational motion of said tube axes about an axis substantially perpendicular to said tube axes.

3. A device according to claim 1 wherein said coupler element permits relative rotation motion of said tube axes about an axis substantially parallel to said tube axes.

4. A device according to claim 1 wherein said central axes of said tubular elements are offset by an angle A and diverge from said first ends thereof.

5. A device according to claim 1 wherein each of said tubular elements includes passageways extending therethrough transverse to said tube axes.

6. A device according to claim 5 wherein said passageways are elongated and extend at least in part in the direction of said tube axes.

7. A device according to claim 1 wherein at least one of said tubular elements further comprises at least one resilient tab extending from said first end in a direction substantially parallel to said tube axes.

8. A device according to claim 1 wherein at least one of said tubular elements further comprises:
   (i) at least one resilient radially extending tab support extending from said first end in a direction substantially perpendicular to said tube axis; and
   (ii) at least one resilient tab extending from said tab support in a direction substantially parallel to said tube axis and toward said second end.

\* \* \* \* \*

UNITED STATES PATENT AND TRADEMARK OFFICE
CERTIFICATE OF CORRECTION

PATENT NO. : 6,562,057 B2
DATED : May 13, 2003
INVENTOR(S) : Ernest Santin

It is certified that error appears in the above-identified patent and that said Letters Patent is hereby corrected as shown below:

<u>Title page,</u>
Item [57], ABSTRACT,
Lines 1-3, delete "Various embodiments of devices to reduce or prevent nasal breathing and snoring are provided." and insert therefore -- Various embodiments of devices to assist nasal breathing and reduce or prevent snoring are provided. --

Signed and Sealed this

Twenty-seventh Day of January, 2004

JON W. DUDAS
*Acting Director of the United States Patent and Trademark Office*